(12) United States Patent
Rezach

(10) Patent No.: US 8,740,947 B2
(45) Date of Patent: Jun. 3, 2014

(54) MULTIPLE LEAD BONE FIXATION APPARATUS

(75) Inventor: Alan Rezach, Atoka, TN (US)

(73) Assignee: Warsaw, Orthopedic, Inc., Warsaw, IN (US)

( * ) Notice: Subject to any disclaimer, the term of this patent is extended or adjusted under 35 U.S.C. 154(b) by 1991 days.

(21) Appl. No.: 11/354,483

(22) Filed: Feb. 15, 2006

(65) Prior Publication Data

US 2007/0233063 A1 Oct. 4, 2007

(51) Int. Cl.
*A61B 17/70* (2006.01)

(52) U.S. Cl.
USPC ............ 606/269; 606/270; 606/275; 606/328

(58) Field of Classification Search
USPC ............ 606/61, 73, 264–275, 300, 301, 305, 606/306, 315–317, 328
See application file for complete search history.

(56) References Cited

U.S. PATENT DOCUMENTS

| | | | |
|---|---|---|---|
| 3,942,405 A * | 3/1976 | Wagner ........................ | 411/386 |
| 4,854,311 A | 8/1989 | Steffee | |
| 4,858,601 A * | 8/1989 | Glisson ........................ | 606/916 |
| 4,959,064 A | 9/1990 | Engelhardt | |
| 5,078,607 A | 1/1992 | Niznick | |
| 5,087,199 A | 2/1992 | Lazarof | |
| 5,176,678 A * | 1/1993 | Tsou ............................ | 606/61 |
| 5,259,348 A | 11/1993 | Vrespa | |
| 5,435,723 A | 7/1995 | O'Brien | |
| 5,527,183 A | 6/1996 | O'Brien | |
| 5,588,838 A | 12/1996 | Hansson | |
| 5,601,553 A | 2/1997 | Trebing | |
| 5,891,145 A * | 4/1999 | Morrison et al. ............ | 606/266 |
| 5,954,722 A | 9/1999 | Bono | |
| 6,090,111 A * | 7/2000 | Nichols ........................ | 606/266 |
| 6,113,601 A * | 9/2000 | Tatar ............................ | 606/266 |
| 6,129,730 A * | 10/2000 | Bono et al. .................. | 606/291 |
| 6,248,105 B1 * | 6/2001 | Schlapfer et al. ............ | 606/266 |
| 6,280,442 B1 * | 8/2001 | Barker et al. ................ | 606/60 |
| 6,298,642 B1 | 10/2001 | Morrison | |
| 6,440,132 B1 * | 8/2002 | Jackson ........................ | 606/308 |
| 6,485,491 B1 * | 11/2002 | Farris et al. .................. | 606/250 |
| 6,547,584 B2 | 4/2003 | Hansson | |
| 6,565,565 B1 * | 5/2003 | Yuan et al. .................... | 606/272 |
| 6,565,566 B1 * | 5/2003 | Wagner et al. ............... | 606/267 |
| 6,602,255 B1 * | 8/2003 | Campbell et al. ............ | 606/290 |
| 6,660,004 B2 * | 12/2003 | Barker et al. ................ | 606/328 |
| 6,716,214 B1 * | 4/2004 | Jackson ........................ | 606/266 |
| 6,905,500 B2 * | 6/2005 | Jeon et al. .................... | 606/270 |
| 6,955,677 B2 | 10/2005 | Dahners | |
| 7,066,937 B2 * | 6/2006 | Shluzas ........................ | 606/86 A |
| 7,144,396 B2 * | 12/2006 | Shluzas ........................ | 606/61 |
| 7,338,491 B2 * | 3/2008 | Baker et al. .................. | 606/308 |
| 7,476,239 B2 * | 1/2009 | Jackson ........................ | 606/266 |
| 7,491,218 B2 * | 2/2009 | Landry et al. ................ | 606/246 |
| 7,513,905 B2 * | 4/2009 | Jackson ........................ | 606/266 |

(Continued)

*Primary Examiner* — Ellen C Hammond

(57) ABSTRACT

An orthopedic bone anchor device is disclosed that includes, in one embodiment, a receiver member, an anchor member and a retaining member. The retaining member may retain the anchor member at least partially in the receiver member. In certain embodiments, the anchor member may have a groove in a head for accommodating part of the retaining member, and/or a multiple lead thread.

20 Claims, 2 Drawing Sheets

(56) References Cited

U.S. PATENT DOCUMENTS

| | | | |
|---|---|---|---|
| 2004/0267264 A1* | 12/2004 | Konieczynski et al. | 606/73 |
| 2005/0049588 A1* | 3/2005 | Jackson | 606/61 |
| 2005/0192571 A1* | 9/2005 | Abdelgany | 606/61 |
| 2006/0009770 A1* | 1/2006 | Speirs et al. | 606/69 |
| 2006/0074419 A1* | 4/2006 | Taylor et al. | 606/70 |
| 2006/0079895 A1* | 4/2006 | McLeer | 606/61 |
| 2006/0100626 A1* | 5/2006 | Rathbun et al. | 606/69 |
| 2007/0093832 A1* | 4/2007 | Abdelgany | 606/61 |
| 2007/0118117 A1* | 5/2007 | Altarac et al. | 606/61 |
| 2008/0086129 A1* | 4/2008 | Lindemann et al. | 606/61 |

* cited by examiner

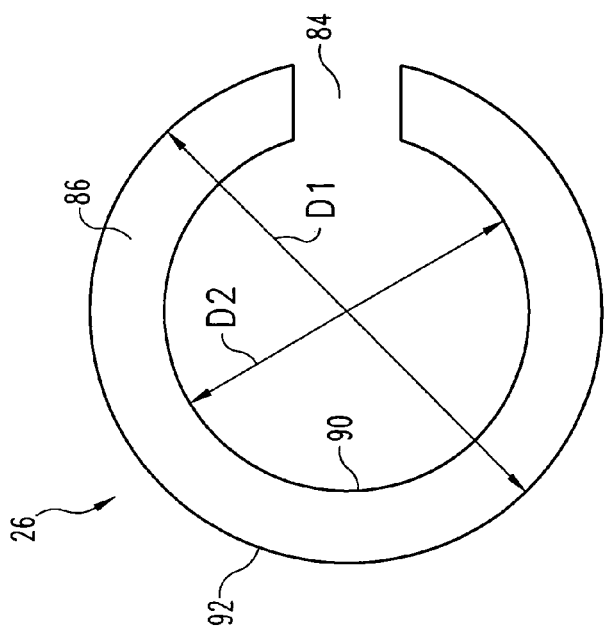
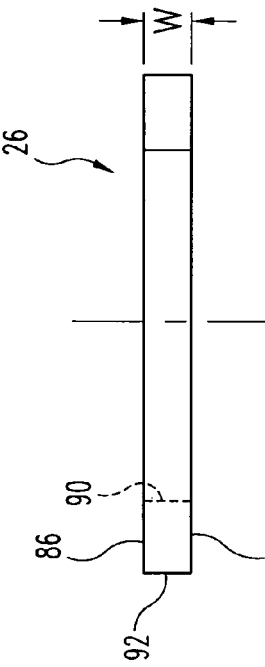
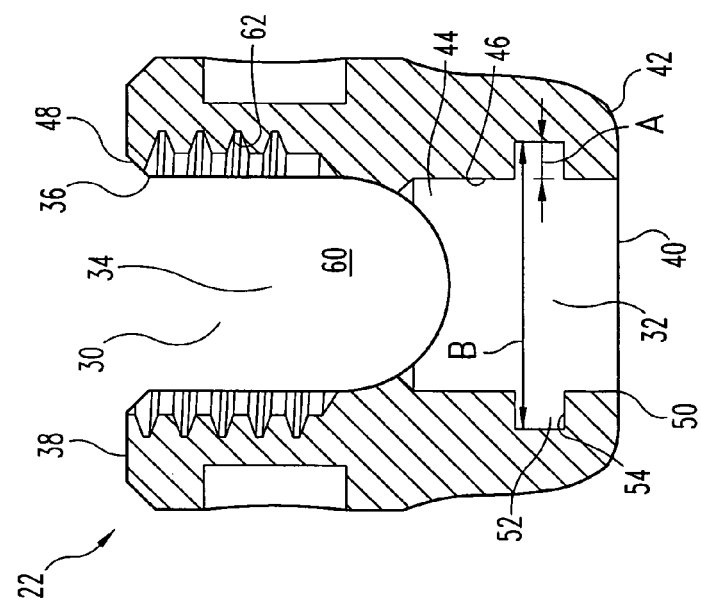
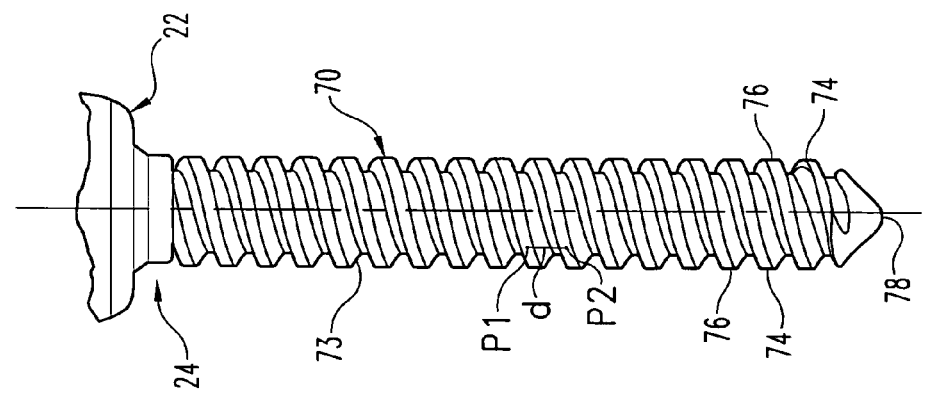

MULTIPLE LEAD BONE FIXATION APPARATUS

The present disclosure relates to devices and implants used in osteosynthesis and other orthopedic surgical procedures. Specifically, the present disclosure includes a bone anchor assembly having a substantially fixed axis.

Several techniques and systems have been developed for correcting and stabilizing damage or malformation of bones, especially the long bones and the spine. In one type of system, an elongated member such as a bendable rod is disposed longitudinally along a length of the bone(s). In spinal applications, the rod may be bent to correspond to the normal curvature of the spine in the particular region being instrumented. For example, the rod can be bent to form a normal kyphotic curvature for the thoracic region of the spine, or a lordotic curvature for the lumbar region. In accordance with such a system, the rod is connected to various vertebrae along a length of the spinal column by way of a number of fixation elements. A variety of hooks, screws, clamps or other fixation elements can be provided which are configured to engage specific portions of the vertebra and other bones.

BRIEF DESCRIPTION OF THE DRAWINGS

FIG. 4 is an enlarged side elevational view of a portion of the embodiment depicted in FIG. 3.

FIG. 5 is an enlarged cross-sectional view of a portion of the embodiment as seen in FIG. 2.

FIG. 6A is a top plan view of a portion of the embodiment seen in FIG. 2.

FIG. 6B is a side elevational view of the portion of the embodiment depicted in FIG. 6A.

DESCRIPTION OF THE ILLUSTRATED EMBODIMENTS

Figure 3:
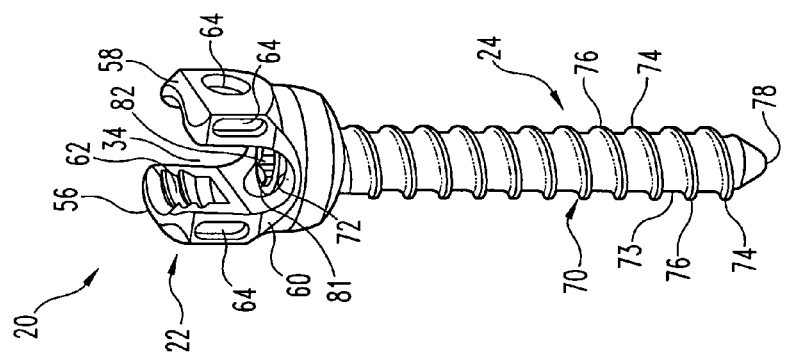
FIG. 3 is a perspective view of the embodiment depicted in FIG. 1.
Figure 2:
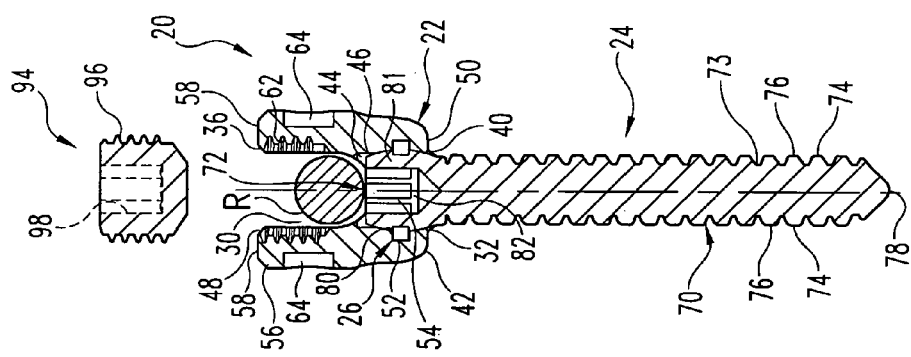
FIG. 2 is a cross-sectional view of the embodiment depicted in FIG. 1, taken along the lines II-II in FIG. 1 and viewed in the direction of the arrows.
Figure 1:
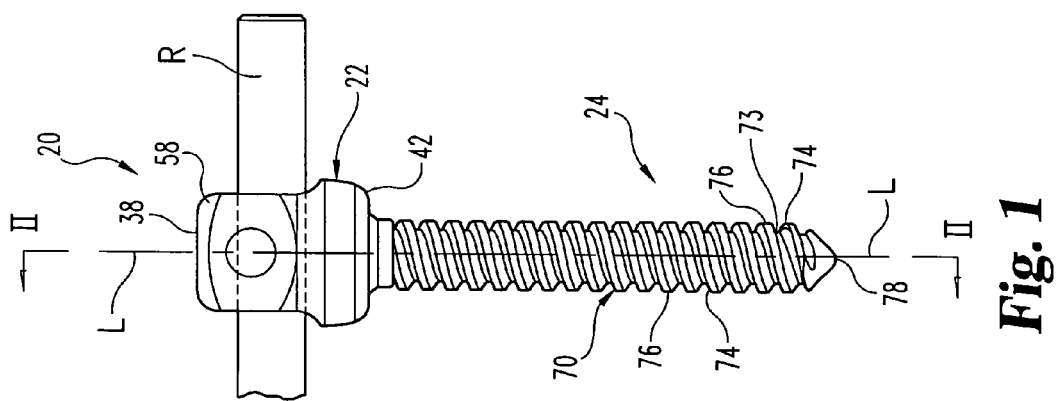
FIG. 1 is a side elevational view of one embodiment of a bone anchor assembly.

For the purposes of promoting an understanding of the principles of the disclosure, reference will now be made to the embodiments illustrated in the drawings and specific language will be used to describe the same. It will nevertheless be understood that no limitation of the scope of the claims is thereby intended, such alterations and further modifications in the illustrated devices, and such further applications of the principles of the disclosure as illustrated therein, being contemplated as would normally occur to one skilled in the art to which the disclosure relates.

Referring generally to the figures, there is shown one embodiment of a bone anchor assembly 20. In the illustrated embodiment, assembly 20 includes a receiver member 22, a bone anchor 24, and a retaining member 26. Assembly 20 can be connected to bone, such as vertebrae, or other tissue and used with an elongated member R such as a spinal rod, bar or other orthopedic construct, as further described below.

In the illustrated embodiment, receiver member 22 defines an upper opening portion 30 and a lower opening portion 32, which may form a single opening 34 extending through receiver member 22 from an upper aperture 36 in top end 38 to a lower aperture 40 in bottom end 42. Lower opening portion 32, in one specific embodiment, includes a chamber 44 defined by a chamber wall 46. Alternatively, upper opening portion 30 and/or lower opening portions 32 can have a variety of configurations, such as each having one or more sections of differing diameter.

Opening 34 is partially surrounded by a chamfered or rounded edge 48 at top end 38 of receiver member 22, and is surrounded by chamfered or rounded edge 50 at the bottom end 42 of receiver member 22. Proximate to bottom end 42, receiver member 22 defines a groove 52 and associated ledge 54 around opening 34. In the illustrated embodiment, groove 52 extends around the entire perimeter of opening 34, although it will be seen that groove 52 could extend only partially around the perimeter of opening 34. Groove 52 has a groove depth A and a groove diameter B.

Receiver member 22 in the illustrated embodiment includes a pair of upright branches 56, 58 between which opening 34 extends. Branches 56, 58 further define a U-shaped channel 60 transverse to opening 34 that communicates with upper portion 30 and lower portion 32 of opening 34, and that accommodates an elongated member R. In a specific embodiment, internal threads 62 are formed in branches 56, 58, and branches 56, 58 are provided with indentations or holes 64, which allow the surgeon to grip receiver member 22 with a forceps, pliers or other appropriate tool (not shown). Internal thread 62 in a specific embodiment is a reverse angle thread, i.e. a thread in which the forward face points down and in toward receiver member 22, as disclosed in commonly-owned U.S. Pat. No. 6,296,642, which is incorporated by reference herein in its entirety. Preferably, a top portion of receiver member 22 (which includes branches 56, 58) is narrower than a bottom portion of receiver member 22, thereby reducing the bulk and profile of receiver member 22.

Bone anchor 24 in the illustrated embodiment is a bone screw having an anchorage portion 70 with a longitudinal axis L and a head portion 72. Anchorage portion 70 is a shaft 73 in the illustrated embodiment that includes two thread crests 74 and 76 beginning at or around tip 78 and extending along anchorage portion 70. In particular embodiments, crests 74 and 76 have the same pitch, and do not intersect on anchorage portion 70. In such embodiments, any two points on crests 74 and 76 that are connected by a line that is coplanar with axis L of anchor 24, e.g. points P1 and P2, the distance d between such points is constant. As a corollary, given two points, one on crest 74 and the other on crest 76, that are separated by distance d, those points will be in phase. The thread configuration illustrated in the drawings and described above may be termed a multiple lead thread or a multiple crest thread. Shaft 73 forms a root for crests 74 and 76 in this embodiment, which has a substantially constant root diameter, and in one particular embodiment the crest diameters of crests 74 and 76 are substantially equal. In other embodiments, the root diameter (i.e. the diameter of shaft 73) may vary along the length of anchorage portion 70, for example by getting larger as one moves from tip 78 toward head portion 72. Likewise, in other embodiments the crest diameters of crests 74 and 76 may be substantially different. Crests 74 and 76 may form a cancellous self-tapping thread, or may be configured in other ways suitable for use in orthopedic implants.

Head portion 72 forms part of a sphere in the illustrated embodiment, though alternative curvate and other configurations may be employed. Head 72 in one particular embodiment includes a groove (which may be a series of grooves) 80 on a side. In the illustrated embodiment in which head portion 72 is a part of a sphere, groove 80 is substantially along a great circle of the sphere that is substantially perpendicular to axis L. Groove 80 may be substantially or completely continuous around the perimeter of head 72, or may have one or more discrete sections, with the surface of head portion 72 adjacent it or between them. An upper surface 81 of head 72 is substantially flat in the illustrated embodiment, and may be in a plane that is substantially perpendicular to axis L and/or parallel to a plane of groove 80. A tool-engaging print 82, with which a tool (not shown) may be engaged to drive anchorage portion 70 into bone and/or other tissue, may be provided in head portion 72. In the illustrated embodiment, print 82 has an axis that is substantially collinear with axis L. Print 82 can be an interior print, as shown in the illustrated embodiment, or an exterior print could be provided, and print 82 may have any of a number of configurations, such as hexagonal, hexalobate, or other known torque-transferring configurations, whether internal or external.

Other embodiments of bone anchor 24 are contemplated as being within the scope of the present disclosure. For example, bone anchor 24 could be a bone-engaging hook rather than a screw. In that embodiment, anchorage portion 70 would be configured with a hook rather than an elongated multiple lead threaded section.

Head 72 of bone anchor 24 is shaped and sized to fit within at least lower portion 32 of opening 28 and chamber 44 of receiver member 22. Specifically, head 72 has a width that is smaller than the width of lower opening portion 32 and chamber 44. As more fully described below, bone anchor 24 is inserted into receiver member 22, with head 72 entering lower opening portion 32 and chamber 44 through bottom end 42 of receiver member 22.

In the illustrated embodiment, retaining member 26 has the form of a C-shaped spring or clip defining a gap 84. Retaining member 26 is shaped substantially as part of a cylinder, having a top surface 86 and a bottom surface 88 that are substantially parallel, and internal surface 90 and external surface 92 that are substantially perpendicular to each of surfaces 86 and 88. In other embodiments, retaining member may be otherwise shaped or configured, as with beveled or rounded portions between internal surface 90 and one or both of surfaces 86 and 88, or between external surface 92 and one or both of surfaces 86 and 88, to facilitate connection of retaining member 26 with receiver member 22 and/or anchor 24, as further described below. As another example, retaining member 26 may be wavy or undulating, providing some spring-like action, rather than substantially flat.

Retaining member 26 has an unloaded or natural outer diameter D1 and inner diameter D2, i.e. diameters measured when retaining member 26 is under no contractive (gap-closing) or expansive (gap-opening) stress. Diameter D1 of retaining member 26, in one embodiment, is less than groove diameter B of groove 52. Further, retaining member 26 has a body width W that is substantially constant throughout the illustrated embodiment of retaining member 26. Body width W of retaining member 26 is greater than groove depth A of groove 52 in the illustrated embodiment. Internal diameter D2 may be slightly smaller than an internal diameter of groove 80 in head 72 of anchor 24. Thus, in one embodiment retaining member 26 is sized and shaped so that it has a gripping fit with head 72, and so that it fits at least partially in groove 52 of receiver member 22. In a particular embodiment, the width of the arms of retaining member 26 is such that a close fit is achieved when retaining member is within grooves 52 and 80.

Apparatus 20 may be assembled by inserting bone anchor 24 and retaining member 26 into receiver member 22 either individually or substantially in one step. For example, retaining member 26 can be inserted into receiver member 22, for example through bottom end 42 by contracting retaining member 26 (making gap 84 smaller) until outer diameter D1 is the same as the diameter of chamber 44 of receiver member 22, and fitted into groove 52 of receiver member 22. Bone anchor 24 can then be inserted, again through bottom end 42 in one embodiment, so that head portion 72 goes through retaining member 26. In this embodiment, head portion 72 may expand retaining member 26 within groove 52 until retaining member 26 enters or snaps into groove 80 of head 72. Alternatively, retaining member 26 could be first fitted at least 20 partially into groove 80 of head 72, so that retaining member 26 can be compressed further into groove 80. The combination of retaining member 26 and anchor 24 can be inserted, for example through bottom end 42 as described above, into receiver member 22, so that retaining member 26 at least partially enters groove 52 of receiver member 22. In other embodiments, bone anchor 24 could be inserted into receiver member 22 so that groove 80 and groove 52 are adjacent, and retaining member 26 can be inserted over anchoring portion 70 of bone anchor 24 and into receiver member 22, so that a part of retaining member 26 enters each of groove 80 of anchor 24 and groove 52 of receiver member 22.

As noted above, in one specific embodiment the groove diameter B of groove 52 is smaller than the outer diameter D1 of retaining member 26 in its natural (i.e., unloaded) condition. Thus, when retaining member 26 is within groove 52, retaining member 26 presses against the walls of groove 52. Alternatively, groove diameter B of groove 52 may be the same size or slightly larger than the natural outer diameter D1 of retaining member 26. In this case, the lower surface 88 of retaining member 26 rests upon ledge 54 of groove 52, and thereby holds retaining member 26 within groove 52. Since groove depth A of groove 52 in this embodiment is less than the body width W of retaining member 26, when retaining member 26 is fitted in groove 52, a portion of retaining member 26 projects into chamber 44 of receiver member 22.

When retaining ring 26 is seated within groove 52 of receiver member 22 and groove 80 of anchor 24, then anchor 24 and receiver member 22 are securely connected with each other. Anchor 24 and receiver member 22 are rotatable with respect to each other substantially around the axis L of anchor 24, making this embodiment a substantially fixed-axis screw. Anchor 24 and receiver member 22, in this embodiment, are limited or prohibited from pivoting with respect to each other about multiple axes and from translation with respect to each other along axis L. Retaining member 26 is held in groove 52 and groove 80, and thus anchor 24 does not pass through retaining member 26 and out of receiver member 22.

Assembly 20 may be assembled (as described above) prior to use in a surgical procedure. In using the illustrated embodiment of assembly 20, anchor 24 of assembly 20 is threaded into an appropriately prepared hole in a bone (not shown). It has been found that multiple crests, such as crests 74 and 76, enable faster threading and better purchase between anchor 24 and bone or other tissue. In embodiments where anchor 24 is a bone hook or other type of implant, drilling a hole in bone and threading the anchor therein may not be necessary. Threaded anchoring portion 70 is inserted into the hole, and an appropriate screwing tool is used with tool-engaging print 82 of bone anchor 24 to thread anchor 24 into the bone. When anchor 24 has been threaded into the bone to the desired depth, receiver member 22 may be rotated around axis L with respect to anchor 24 as may be desired by a surgeon.

Once anchor 24 and receiver member 22 are positioned, an elongated member R such as a spinal rod, connector, or other orthopedic surgical implant is coupled with assembly 20. Elongated member R is placed in channel 60 of receiver member 22, and may contact top surface 81 of anchor 24. A compression member 94, such as a set screw, is inserted into receiver member 22 (e.g. by threading into threads 62 of the illustrated embodiment of receiver member 22) and down onto elongated member R. Compression member 94, in one embodiment, has external threads 96 and a print 98 for applying torque, and in a specific embodiment may be a break-off set screw. In a particular embodiment, thread 96 is a reverse angle thread compatible with the reverse angle embodiment of thread 62 of receiver member 22, described above. Alternatively, where receiver member 22 is externally threaded, compression member 94 could be an internally-threaded nut, or compression member 94 could be a clamp, spring-loaded, or other type of apparatus that can apply pressure to elongated member R.

As compression member 94 is tightened, elongated member R is forced downward against surface 81 of head 70 of bone anchor 24. Head 70 is thereby clamped between retaining member 26 and elongated member R. In this way, bone anchor 24 is locked with respect to elongated member R and the remainder of assembly 20.

Alternatively, assembly 20 can be assembled during the surgical procedure. Bone anchor 24, with retaining ring 26 positioned in groove 52 of receiver member 22 or groove 80 of anchor 24, is inserted into the bone. Receiver member 22 is then pressed down onto head 70 of anchor 24, forcing retaining ring 26 into the other of grooves 52 and 80, as described above. After assembly 20 is assembled in this fashion, an elongated member (e.g. rod R) is loaded into receiver member 22 and locked as previously described.

Materials useful for the embodiments described above include stainless steel and titanium, although a variety of sturdy biocompatible materials could be used to accomplish the desired orthopedic surgical goals.

While the disclosure has been illustrated and described in detail in the drawings and foregoing description, the same is to be considered as illustrative and not restrictive in character, it being understood that only the preferred embodiment has been shown and described and that all changes and modifications that come within the spirit of the disclosure are desired to be protected.

What is claimed is:

1. An orthopedic medical apparatus comprising:
a receiver member having a channel for receiving at least a portion of an elongated member and terminating at a bottom surface, a chamber and a groove positioned in said chamber, said groove including an upper end positioned below said bottom surface of said channel;
a screw member having a head portion and a shaft portion, said shaft portion having a longitudinal axis, a first thread crest having a pitch and a second thread crest that does not contact said first crest and has a pitch substantially equal to said pitch of said first thread crest, said head portion of said screw member having a groove; and
a ring member in at least part of said groove of said receiver member and in at least part of said groove of said screw member.

2. The apparatus of claim 1, wherein said groove of said screw member is substantially in a single plane, and said plane is substantially perpendicular to said longitudinal axis.

3. The apparatus of claim 1, wherein said head portion forms at least part of a sphere, and said groove of said screw member forms at least part of a great circle of said sphere.

4. The apparatus of claim 1, wherein said groove of said screw member is substantially in a single plane, and said head portion has a substantially flat portion substantially parallel to said plane.

5. The apparatus of claim 1, wherein said first thread crest and said second thread crest have substantially the same crest diameter.

6. The apparatus of claim 1, wherein said shaft portion forms a substantially constant root diameter between each of said thread crests.

7. The apparatus of claim 1, wherein positioning of said ring member in at least part of said groove of said receiver member and in at least part of said groove of said screw member limits translational and pivotal movement of said receiver member relative to said screw member while permitting rotational movement of said receiver member about said head portion of said screw member.

8. An orthopedic medical apparatus comprising:
a receiver member having a channel for receiving at least a portion of an elongated member and terminating at a bottom surface, a chamber and a groove positioned in said chamber, said groove including an upper end positioned below said bottom surface of said channel;
an anchor member having a head portion and a bone-anchoring portion, said head portion having a groove; and
a ring member in at least part of said groove of said receiver member and in at least part of said groove of said anchor member.

9. The apparatus of claim 8, wherein said bone-anchoring portion includes a threaded shaft.

10. The apparatus of claim 9, wherein said threaded shaft has multiple leads.

11. The apparatus of claim 10, wherein said multiple leads have substantially the same pitch.

12. The apparatus of claim 8, wherein said bone-anchoring portion includes a hook.

13. The apparatus of claim 8, wherein said bone-anchoring portion has a longitudinal axis, and wherein said groove of said screw member is substantially in a single plane, and said plane is substantially perpendicular to said axis.

14. The apparatus of claim 8, wherein said head portion forms at least part of a sphere, and said groove of said screw member forms at least part of a great circle of said sphere.

15. The apparatus of claim 8, wherein said groove of said anchor member is substantially in a single plane, and said head portion has a substantially flat portion substantially parallel to said plane.

16. The apparatus of claim 8, wherein positioning of said ring member in at least part of said groove of said receiver member and in at least part of said groove of said anchor member limits translational and pivotal movement of said receiver member relative to said anchor member while permitting rotational movement of said receiver member about said head portion of said anchor member.

17. An orthopedic medical apparatus, comprising:
a receiver member having an axial opening and a channel transversely intersecting said axial opening and terminating at a bottom surface, said channel configured to receive at least a portion of an elongated member, and said axial opening defined by an inner wall of a chamber having a first groove extending at least partially about a perimeter of said axial opening and including an upper end positioned below said bottom surface of said channel;
an anchor member including a head portion and a bone-anchoring portion, said head portion having a second groove extending at least partially about a perimeter of said head portion; and
a retaining member positioned in at least a portion of said groove of said receiver member and in at least part of said groove of said anchor member to limit translational and pivotal movement of said receiver member relative to said anchor member.

18. The apparatus of claim 17, wherein said bone-anchoring portion comprises a threaded shaft having multiple leads with substantially the same pitch.

19. The apparatus of claim 17, wherein said head portion forms at least part of a sphere, and said second groove forms at least part of a great circle of said sphere.

20. The apparatus of claim 17, wherein said retaining member permits rotational movement of said receiver member about said head portion of said anchor member.

* * * * *